(12) United States Patent
Fierlbeck et al.

(10) Patent No.: US 9,072,557 B2
(45) Date of Patent: Jul. 7, 2015

(54) MODULAR HOOK PLATE ASSEMBLY

(75) Inventors: Johann Fierlbeck, Oberdorf (CH); Alfred Niederberger, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 201 days.

(21) Appl. No.: 13/369,905

(22) Filed: Feb. 9, 2012

(65) Prior Publication Data

US 2013/0041375 A1   Feb. 14, 2013

Related U.S. Application Data

(60) Provisional application No. 61/449,311, filed on Mar. 4, 2011.

(51) Int. Cl.
*A61B 17/80* (2006.01)

(52) U.S. Cl.
CPC ......... *A61B 17/8061* (2013.01); *A61B 17/8042* (2013.01); *A61B 17/8033* (2013.01); *A61B 17/80* (2013.01); *A61B 17/809* (2013.01)

(58) Field of Classification Search
CPC ........... A61B 17/6425; A61B 17/8061; A61B 17/8042; A61B 17/8033; A61B 17/80; A61B 17/809
USPC ...................................... 606/279–299, 70, 71
See application file for complete search history.

(56) References Cited

U.S. PATENT DOCUMENTS

| 5,616,144 | A  | * | 4/1997  | Yapp et al. ................ 606/280 |
| 5,674,222 | A  |   | 10/1997 | Berger et al. |
| 5,928,234 | A  | * | 7/1999  | Manspeizer ................ 606/54 |
| 6,129,728 | A  | * | 10/2000 | Schumacher et al. ......... 606/71 |
| 6,929,646 | B2 | * | 8/2005  | Gambale .................. 606/71 |
| 8,425,513 | B2 | * | 4/2013  | Frankle et al. ............ 606/63 |
| 2002/0183752 | A1 | * | 12/2002 | Steiner et al. ............ 606/69 |
| 2004/0102778 | A1 | * | 5/2004  | Huebner et al. ........... 606/71 |
| 2005/0015089 | A1 | * | 1/2005  | Young et al. ............. 606/69 |
| 2005/0124996 | A1 | * | 6/2005  | Hearn .................... 606/71 |
| 2007/0233112 | A1 | * | 10/2007 | Orbay et al. ............. 606/69 |
| 2009/0012569 | A1 |   | 1/2009  | Dall et al. |
| 2009/0275987 | A1 | * | 11/2009 | Graham et al. ............ 606/280 |
| 2011/0218534 | A1 | * | 9/2011  | Prandi et al. ............ 606/71 |

FOREIGN PATENT DOCUMENTS

| CH | 578 864 | 8/1976 |
| EP | 1 743 586 | 1/2007 |
| WO | 2010/061410 | 6/2010 |

* cited by examiner

*Primary Examiner* — David Bates
*Assistant Examiner* — Samuel Hanna
(74) *Attorney, Agent, or Firm* — Fay Kaplun & Marcin, LLP

(57) ABSTRACT

A hook plate assembly includes a bone plate extending along a longitudinal axis from a first end to a second end and including an upper surface facing away from a bone, a bone contacting surface, a plate hole extending therethrough from the upper surface to the bone contacting surface and a connection section arranged at the second end. The plate hole is sized and shaped to receive a bone fixation element therethrough in combination with a hook including a connecting portion configured to connect the hook to the connection section of the bone plate and a fastening element releasably coupling the hook to the bone plate.

25 Claims, 6 Drawing Sheets

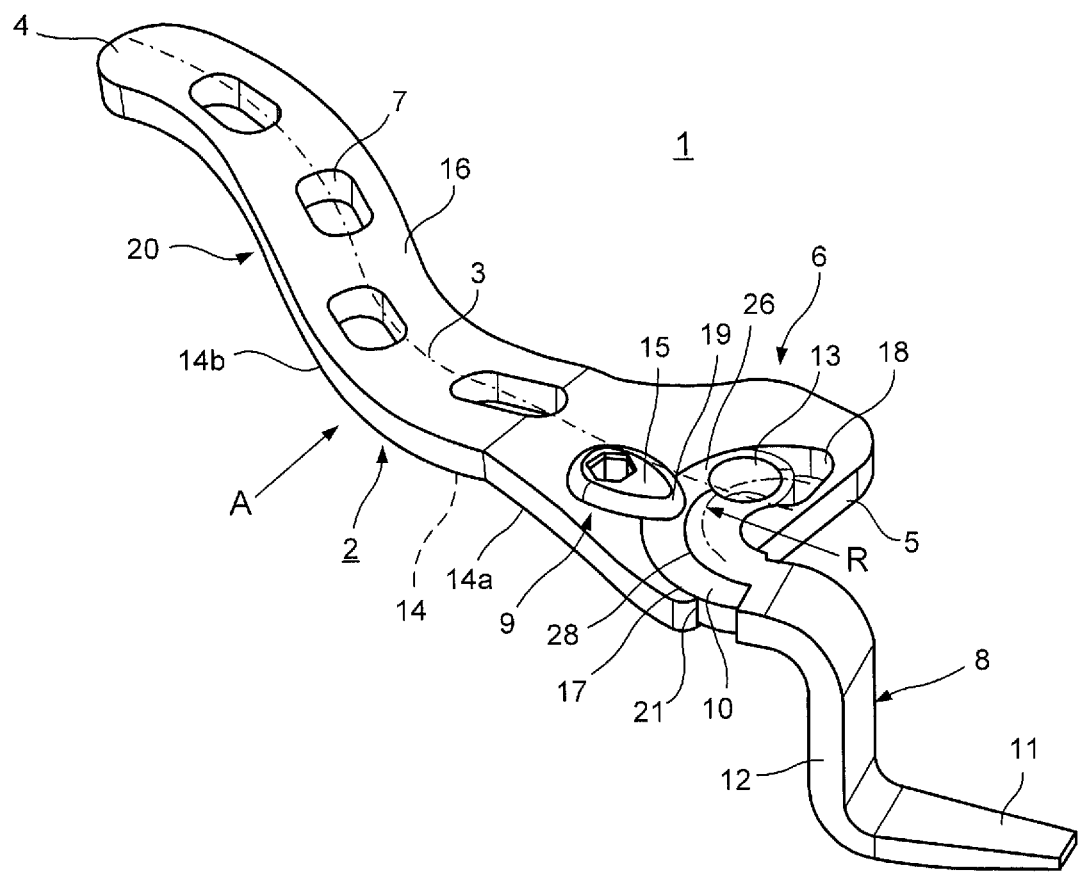
F I G. 1

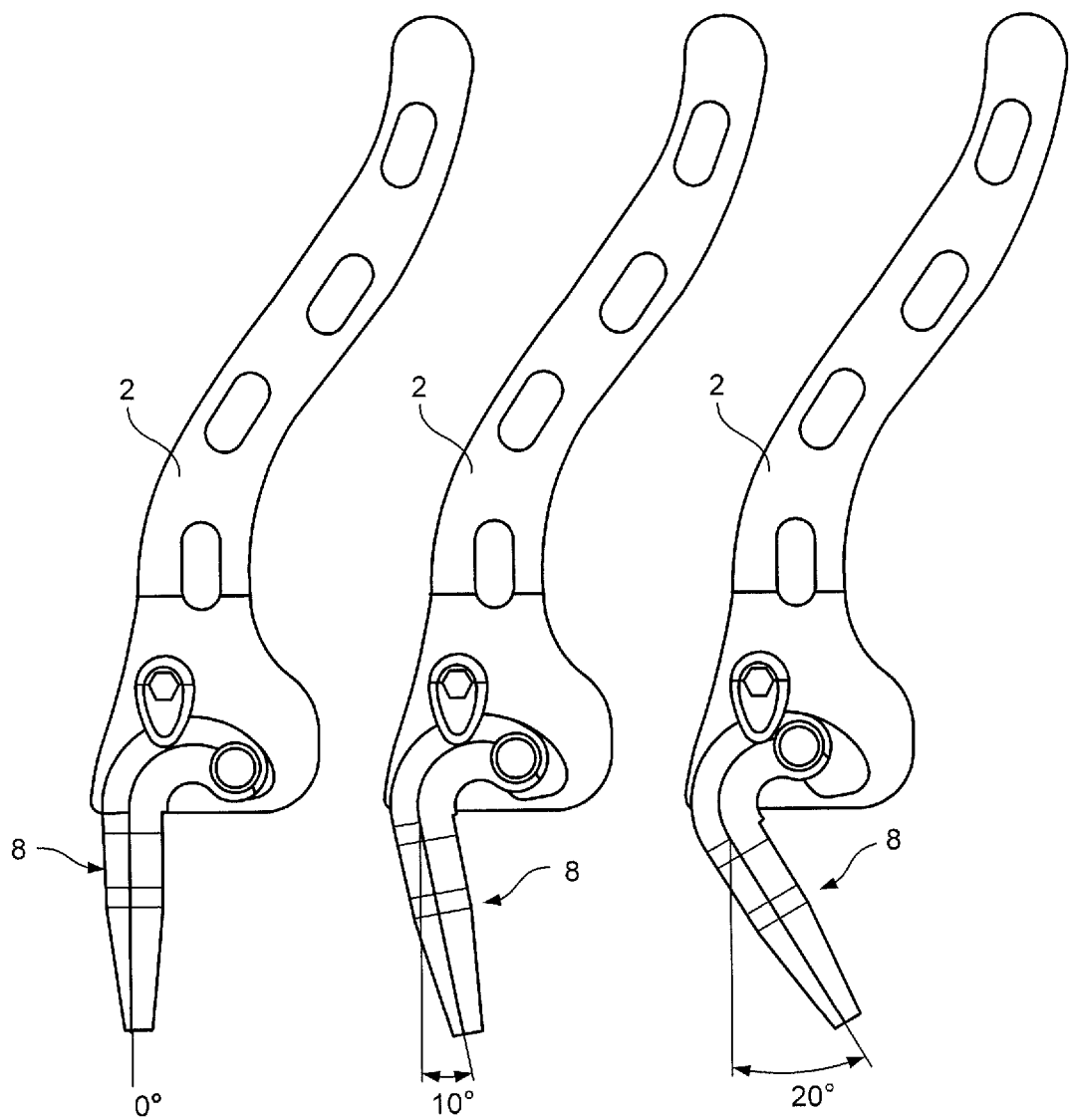

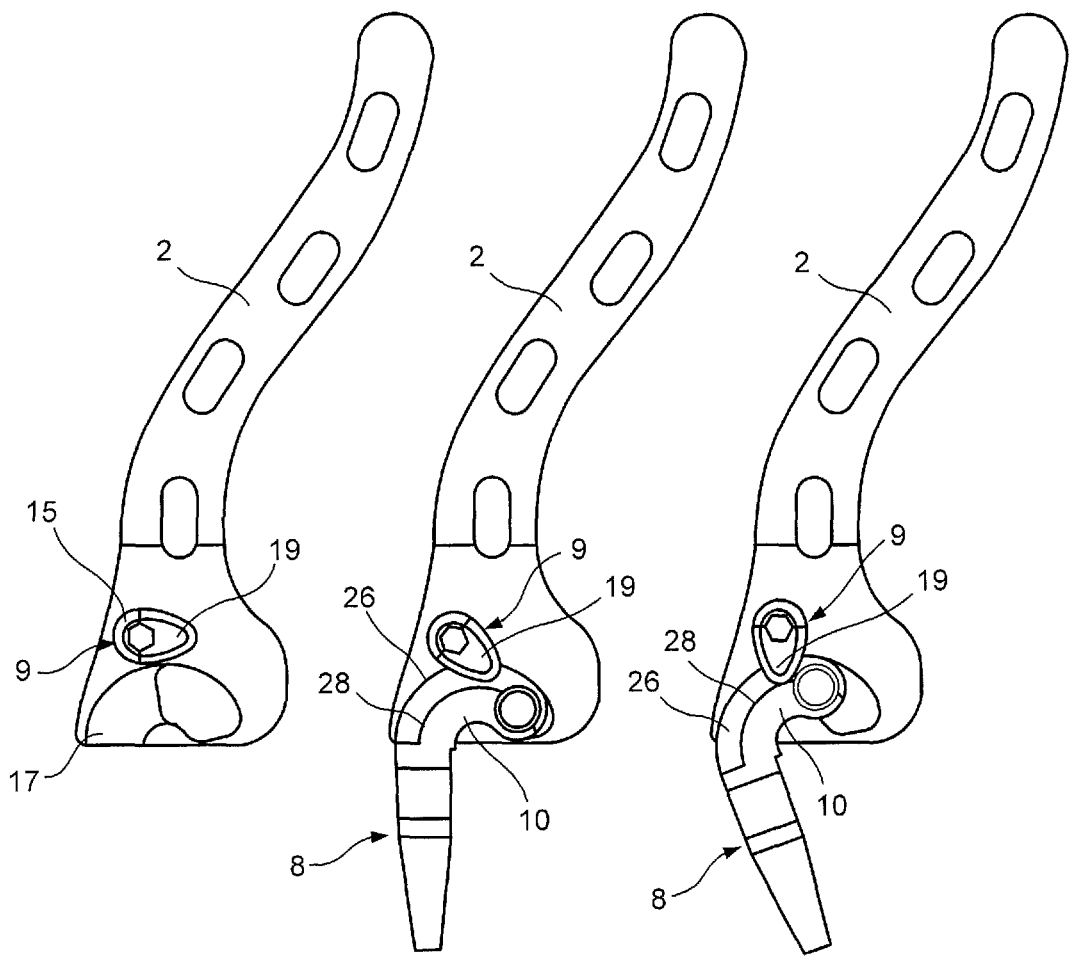
F I G. 5a   F I G. 5b   F I G. 5c

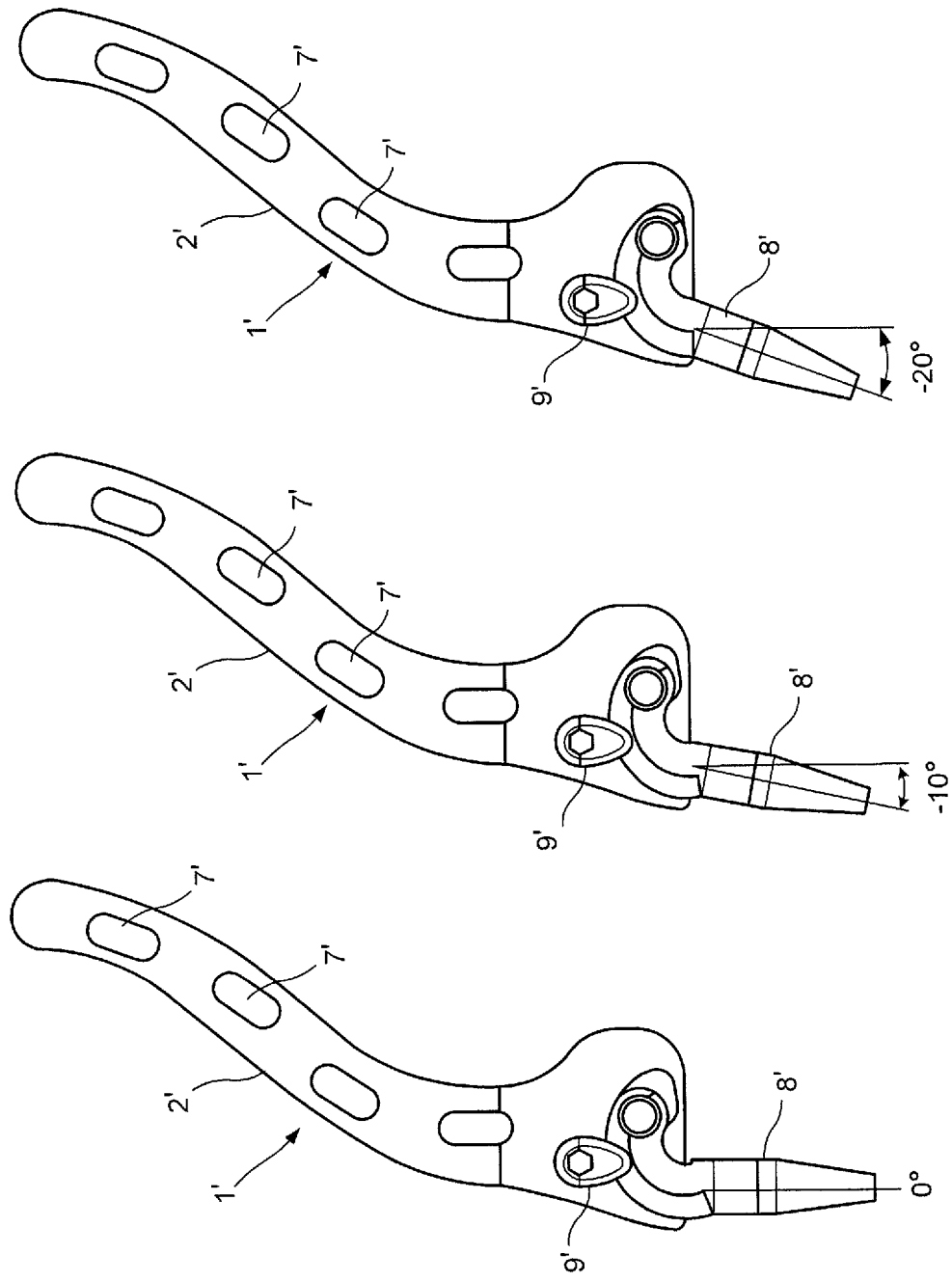

MODULAR HOOK PLATE ASSEMBLY

PRIORITY CLAIM

The present application claims priority to U.S. Provisional Application Ser. No. 61/449,311 filed on Mar. 4, 2011 and entitled "Modular Hook Plate Assembly," the entire disclosure of which is incorporated herein by reference.

FIELD OF THE INVENTION

The present invention generally relates to a surgical implant and methods for treating a bone using the surgical implant. More particularly, the present invention relates to a modular hook plate assembly and methods for stabilizing bony structures and/or dislocations. Exemplary embodiments of the present invention relate to a kit comprising a bone plate and one or more hooks as well as a method for stabilizing clavicular fractures and/or dislocations of the acromioclavicular joint in either an open or minimally invasive procedure.

BACKGROUND

Antero-posterior stabilization of the acromioclavicular joint (AC-joint) is generally maintained via the ligamentum acromioclaviculare and parts of the trapezius and deltoideus muscle. Cranial stabilization is generally maintained via the conoid ligament and the trapezoid ligament (between the coracoid and the clavicle). A fall onto the shoulder with a direct force to the clavicle or on the outstretched arm is a common cause for fractures of the bone or ruptures of the stabilizing soft tissues. Simple fractures or minor AC luxations are treated conservatively. However, more complex fractures such as, for example, Neer type II, Jäger and Breitner type II and acromio-clavicular joint dislocation types such as Tossy III and Rockwood III to V are treated operatively. The Neer and the Jäger and Breitner types involve a bone fracture while the Tossy and Rockwood types involve ruptures of the ligaments without bone fractures.

Various types of fixation techniques and procedures exist for the treatment of these dislocations, which may be divided into four basic principles:

1. Acromio-clavicular repairs (Fixation between the acromion and the distal clavicle);
2. Coraco-clavicular repairs (Fixation between the coracoid and the distal clavicle);
3. Distal clavicle excision; and
4. Dynamic muscle transfers.

Acromio-clavicular fixation may be performed using a clavicle hook plate and variations thereof such as, for example, the Balser plate and the Wolter plate. Currently, the hook plate is used to treat clavicle fractures associated with ruptures of the conoid ligament and trapezoid ligament. The hook plate may be configured in either a left or right version and is commonly formed with three different hook depths. The plate is used to join two bone fragments while the hook is placed under the acromion and used to pull the clavicle to a normal position generally maintained by the ligaments.

However, many patients treated with a hook plate show a phenomenon called "hook migration" in which the hook moves in a cranial direction during healing. When the hook moves in a cranial direction, the hook penetrates the subacromial roof causing osteolysis.

Currently, the only solution to stop erosion and prevent osteolysis is to remove the osteosynthesis device early and hope that the bone fragments have consolidated. Thus, a major drawback of existing hook plates is the occurrence of osteolysis because of the hook being pressed against the AC-roof, which may lead to early removal of the plate even when the fracture has not healed completely. A hook plate with a larger hook would result in subacrominal impingement.

As discussed above, a misplaced hook will begin to erode the acromion. In some situations, even a correctly placed hook may eventually result in erosion. In these situations, the clavicle hook plate must be removed after 3 months. After approximately three months the ruptured ligaments have healed but the fracture may still be unstable. Thus, the surgeon may have to make the difficult decision of either leaving the plate inside the patient and risking further damage to the acromion or removing the plate early to prevent harm to the acromion while risking a new fracture.

SUMMARY OF THE INVENTION

It is an object of the present invention to provide a device and a method for treatment of fractures at the lateral end of the clavicle, which permits correct restoration of the height of the clavicle relative to the acromion while minimizing the risk of damaging the acromion.

The present invention relates to a hook plate assembly comprising: A) a bone plate extending along a longitudinal axis from a first end to a second end and including an upper surface, a bone contacting surface, one or more plate holes for receiving bone screws extending therethrough and a connection section terminally arranged towards the second end; and B) a hook connectable to the connection section. Further, the hook plate assembly comprises a fastening element which permits in situ attachment and/or detachment of the hook from the bone plate.

One of the advantages of the hook plate according to the present invention is that the hook can be assembled and disassembled in situ. Thus, after three months, the hook may be removed from the patient to minimize the risk of osteolysis of the acromion while the bone plate remains fixed to the bone. The bone plate may then be removed after approximately one year, allowing the fracture to fully heal without risking a further fracture of the clavicle.

In one exemplary embodiment of the hook plate assembly, the fastening element, when in a first position, permits the hook to be coupled to the bone plate. When the fastening element is in a second position, the hook is coupled to the bone plate such that the hook is rotatable relative to the bone plate within a predetermined range of angulation. When the fastening element is in a third position, the hook is fixed in a desired position relative to the bone plate via, for example, a friction fit. The hook may be rotatable relative to the bone plate at an angle ranging from between, for example, 0° and 20° in an antero-posterior direction so that the surgeon may place the hook in a position in which the hook has maximum contact with the bone surface. This distributes the load exerted from the hook onto the acromion over a wider area to reduce the risk of occurrence of osteolysis.

In another exemplary embodiment of the hook plate assembly, the hook includes a through hole in a part of the hook overlapping the plate. Thus, a bone screw may be inserted through the through hole and a corresponding aperture in the bone plate to reinforce the fixation of the hook to the bone plate and to the clavicle.

In a further exemplary embodiment of the hook plate assembly, a thickness of the bone plate is a maximum of about 3.5 mm, but preferably a maximum of about 3.0 mm. For example, the thickness may be about 2.5 mm. The hook plate may be placed on a surface of the clavicle, which is only covered by a thin layer of soft tissue. A thin bone plate reduces discomfort and pain for the patient and prevents irritation of the surrounding soft tissue.

In a further exemplary embodiment of the hook plate assembly, the hook may have a raised section. The thickness of the hook may be a maximum of about 3.0 mm, but preferably about 2.5 mm. For example, the hook may have a thickness of about 2.0 mm. Preferably, the hook comprises a raised section with a thickness of between 0.1 to 0.3 mm, where the thickness is in addition to the thickness of the hook.

In yet a further exemplary embodiment of the hook plate assembly, the hook is attachable to the bone plate within a portion of the bone plate such that the height of the implant is not increased at the connection section where the hook is attached to the bone plate.

In another exemplary embodiment of the hook plate assembly, the hook includes a plastic coating thereover. The plastic coating reduces friction and optimizes the force distribution between the bone and the implant to minimize the danger of osteolysis.

In another exemplary embodiment of the hook plate assembly, a depth T of the hook is a maximum of about 20 mm. For example, the depth T may be in the range of about 18 mm to about 12 mm. Since the hook is removably attachable to the bone plate, modular hooks may be provided, each hook with a different hook depth such as, for example, about 12 mm, about 15 mm and about 18 mm. Further, modular hooks with different hook bendings may be provided. The hook has an angle of bending X which may vary between about 60° and about 120°.

In yet another exemplary embodiment of the hook plate assembly, a length L of the hook is a maximum of about 35 mm.

In yet another exemplary embodiment of the hook plate assembly, the hook is rotatable relative to the bone plate about an axis of rotation extending through the bone contacting surface, preferably orthogonal to the bone contacting surface. A rotatable hook remedies the disadvantage of a non-articulated hook in which either the hook is not adjusted in a position relative to the acromion where a damage of the acromion is minimized, or the hook is correctly positioned below the acromion but the plate is not aligned on the bone. Therefore, the hook plate assembly permits both minimization of the risk of damage to the acromion and the correct positioning of the bone plate.

In still another exemplary embodiment of the hook plate assembly, the bone plate has a longitudinal section extending towards the first end of the bone plate, wherein the bone plate is bent or angled when viewed in a front view. The bone plate may be bent or angled at an angle of about 12° between the longitudinal section and the connection section.

In a further exemplary embodiment of the hook plate assembly, the hook is C-shaped or S-shaped.

In a further exemplary embodiment of the hook plate assembly, the fastening element is a screw including a head having a maximum height of about 1.5 mm to minimize the overall height of the hook plate. For example, the height of the head may be about 1.0 mm.

In a further exemplary embodiment of the hook plate assembly, the connection section of the bone plate has a recess configured and dimensioned to receive a connecting portion of the hook. In a preferred embodiment the connecting portion protrudes from the upper surface.

In yet a further exemplary embodiment of the hook plate assembly, the recess is circularly curved and has a middle radius R. The recess may be circularly curved in a plane parallel to the bone contacting surface of the bone plate. The curved recess provides an articulated connection between the bone plate and the hook without requiring a hinge pin so that the hook plate assembly may have a smaller thickness.

In again a further exemplary embodiment of the hook plate assembly, the connecting portion of the hook is correspondingly circularly curved with the middle radius R in a plane parallel to the bone contacting surface of the bone plate.

In still a further exemplary embodiment of the hook plate assembly, the hook is rotatable relative to the bone plate up to about 20°. Due to the relatively small angular range of rotation, the articulation between the bone plate and the hook can be configured by arranging a portion of the hook curvedly sliding on the bone plate resulting in a minimum height of the articulation.

In another exemplary embodiment of the hook plate assembly, the hook has a tip portion, wherein the hook is curved in a plane orthogonal to the bone contacting surface such that the tip portion protrudes from the second end of the bone plate parallel to or at an acute angle relative to the longitudinal axis of the bone plate so that the hook may be slid under the acromion.

In another exemplary embodiment of the hook plate assembly, the bone plate has an aperture penetrating through the connection section for receiving a bone screw so that an additional bone screw may be inserted through the through hole in the hook and the aperture in the connection section of the bone plate to reinforce the connection between the hook and the plate as well as between the hook plate assembly and the bone.

In yet another exemplary embodiment of the hook plate assembly the aperture is located within the recess and is circularly curved with the radius R.

In yet another exemplary embodiment of the book plate assembly, the hook is three-dimensionally curved.

In still another exemplary embodiment of the hook plate assembly, the one or more plate holes are elongated holes having a long axis extending along the longitudinal axis of the bone plate, and preferably having an internal thread at one end of the long axis.

In yet another exemplary embodiment of the hook plate assembly—in a top view—the bone plate is S-shaped or C-shaped so that the bone plate corresponds to the shape of the bone (e.g., the clavicle which is S-shaped). If the bone plate is very short and has only one or two plate holes, the bone plate may be C-shaped.

According to a further aspect of the present invention, a kit comprises a bone plate according to the invention and two or more hooks with a different hook shape. Some of the advantages of the kit according to the invention are:

- a hook with a suitable shape for the particular anatomy of the patient can be selected;
- a modular hook may be inserted into the body via a minimally invasive surgery by first positioning the plate along the bone and then attaching the hook to the plate in situ; and
- the modular hook allows the implant assortment to be reduced. Instead of having three hook sizes and four plate lengths which sums up to 12 different plates, the modular system allows the same variety with only seven implant parts. Smaller hook sizes, which were carefully avoided thus far due to the large assortment of different implants, are therefore also possible.

In accordance with another aspect, the present invention provides a method for treating fractures of the lateral end of the clavicle using a hook plate assembly according to the invention. The method comprises the steps of: a) forming a small incision near the lateral end of the clavicle; b) reducing the fracture and/or the dislocation; c) selecting a hook with an appropriate hook size; d) sliding the bone plate under the skin along the clavicle; e) producing small incisions in the skin to advance bone screws through the plate holes in the bone plate and into the clavicle; f) advancing one or more bone screws through the plate holes in the bone plate and into the clavicle; d) connecting the hook to the bone plate; g) turning the fastening element from the first position to the second position to prevent disengagement of the hook; h) positioning the tip portion of the hook below the acromion by rotating the hook relative to the bone plate until an optimal fit with the acromion is achieved; i) moving the fastening element from the second position to the third position to fix the hook relative to the bone plate; and j) closing the incision. The fastening element is pre-operatively attached to the plate such that the fastening element is movable between the first and second positions. Pre-operative attachment of the fastening element prevents the small fastening element from becoming lost during implantation thereof.

According to a further aspect of the present invention, there is provided a method for treating fractures at the lateral end of the clavicle using a hook plate assembly according to the invention comprising the steps of: 1) forming a larger incision near the top of the lateral end of the clavicle; 2) reducing the fracture and/or the dislocation and selecting an appropriate hook size; 3) positioning the hook, which is connected to the bone plate with the fastening element in the third position, under the acromion and pressing the bone plate onto the clavicle; 4) advancing bone screws through the plate holes in the bone plate and into the clavicle; and 5) closing the incision.

In an exemplary embodiment, the method further comprises, before step 5), the substeps of:
  turning the fastening element to the second position;
  rotating the hook to position the tip portion of the hook under the acromion in an optimal position; and
  moving the fastening element to the third position to fix the hook relative to the bone plate.

In another exemplary embodiment, the method further comprises the step of advancing an additional bone screw into the clavicle through the through hole in the hook and the aperture in the bone plate.

For example, and without limitation, the hook plate assembly according to invention may be used for treatment of fractures of the lateral end of the clavicle.

BRIEF DESCRIPTION OF THE DRAWINGS

Exemplary embodiments of the present invention will be described by way of the following description and with reference to the accompanying drawings in which:

FIG. 1 illustrates a perspective view of a hook plate assembly according to an exemplary embodiment of the present invention;

FIGS. 4a-4c illustrate a top plan view of the connection section of the bone plate according to the hook plate assembly of FIG. 1, with the hook at different angles with respect to the bone plate;

FIGS. 5a-5c illustrate a top plan view of the connection section of the bone plate according to the hook plate assembly of FIG. 1, with the fastening element in different positions during implantation of the hook; and FIGS. 6a-6c illustrate a top plan view of a hook assembly according to a further embodiment of the present invention, with a hook at different angles with respect to a bone plate.

DETAILED DESCRIPTION

Figure 2:
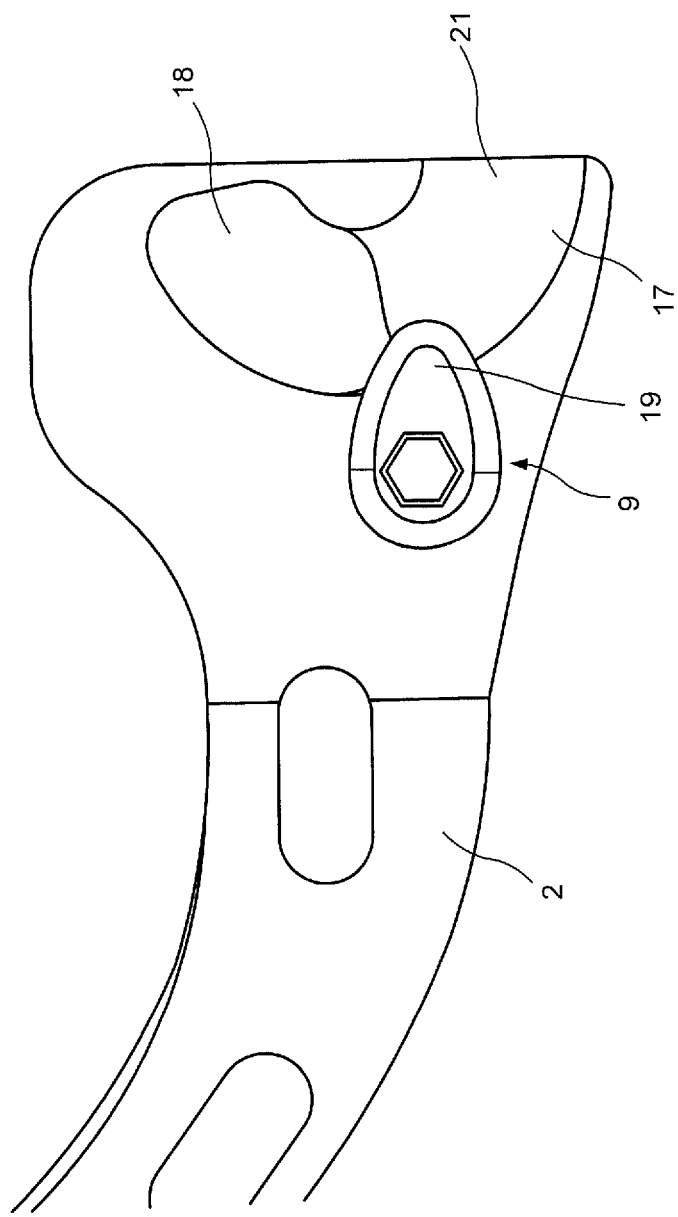
FIG. 2 illustrates a magnified top view of a connection section of a bone plate according to the hook plate assembly of FIG. 1.

The present invention may be further understood with reference to the following description and the appended drawings, wherein like elements are referred to with the same reference numerals. The present invention relates to a device for treating fractures and, in particular, to a clavicle fracture. Exemplary embodiments of the present invention describe a hook plate assembly comprising a bone plate sized and shaped to be positioned along a clavicle and a hook attachable to the bone plate.

FIGS. 1 to 5 illustrate an embodiment of the hook plate assembly 1 comprising a bone plate 2 sized and shaped to be attached to a lateral portion of a clavicle via a bone fixation element such as a bone screw, and a hook 8 attachable to the bone plate 2 to be positioned under the acromion and a fastening element 9 to rigidly fix the hook 8 to the bone plate 2.

The bone plate 2 extends along a longitudinal axis 3 from a first end 4 to a second end 5 and includes an upper surface 16 facing away from the bone, a bone contacting surface 14 and one or more plate holes 7 extending therethrough from the upper surface 16 to the bone contacting surface 14 for receiving bone screws therein. The bone plate 2 has a longitudinal section 20 extending towards the first end 4 of the bone plate 2 and a connection section 6 extending towards the second end 5. The connection section 6 has a width that is larger than a width of the longitudinal section 20. Upon implantation of the bone plate 2, the connection section 6 lies over a lateral end of the clavicle and the hook 8 is connectable thereto.

The bone plate 2 is sized and shaped to be positioned along the clavicle. For example, when viewed in a direction substantially perpendicular to one of the upper and bone contacting surfaces 16, 14, the longitudinal section 20 of the bone plate 2 may be substantially S-shaped including two bends along a length thereof, in a plane substantially parallel to one of the upper and bone contacting surfaces 16, 14—so that its shape is adapted to that of the clavicle. Alternatively, if the bone plate 2 is shorter so that the bone plate 2 is sized to be positioned along only a portion of the clavicle, the longitudinal section 20 may be substantially C-shaped—i.e., including only one bend along a length thereof, in a plane substantially parallel to one of the upper and bone contacting surfaces.

Further, when the bone plate 2, is viewed in a direction of arrow A as shown in FIG. 1, the longitudinal section 20 may be bent or angled relative to the connection section at an angle of approximately 12° to facilitate positioning of the bone plate 2 on the clavicle.

As shown in FIGS. 1 and 2, the connection section 6 of the bone plate 2 includes a recess 17 along the upper surface 16, configured and dimensioned to receive a connecting portion 10 of the hook 8 therein so that the connecting portion 10 protrudes slightly from the upper surface 16 of the bone plate 2. The recess 17 may, for example, be circularly curved with a middle radius R such that the concave side of the recess 17 is directed towards the second end 5 of the bone plate 2. Thus, the recess 17 is circularly curved in a plane parallel to the bone contacting surface 14 of the bone plate 2. Further, the circularly curved recess 17 is open to the second end 5 at an opening 21 so that a remaining length of the hook 8 may extend past the second end 5 of the bone plate 2 in a lateral direction to engage the acromion.

The recess 17 may include an aperture 18 extending through the bone plate 2 along a portion thereof for receiving a bone screw. The aperture 18 may be located within the recess 17 along a portion thereof such that the aperture may share the same radius R as the recess 17.

The longitudinal section 20 of the bone plate 2 may include a plurality of plate holes 7 configured as elongated holes with their long axes extending along the longitudinal axis 3 of the bone plate 2. In one exemplary embodiment, the bone plate 2 includes four plate holes 7. It will be understood by those of skill in the art, however, that the bone plate 2 may include any number of plate holes 7 so long as the plate holes 7 provide a desired level of fixation to the bone. In an alternative embodiment, the plate holes 7 may be combination holes including an internal thread along one end thereof. The internal thread may, for example, extend over more than 180°. The portion of the plate hole 7 including the thread may be substantially cylindrical or conical as those skilled in the art will understand.

Figure 3:
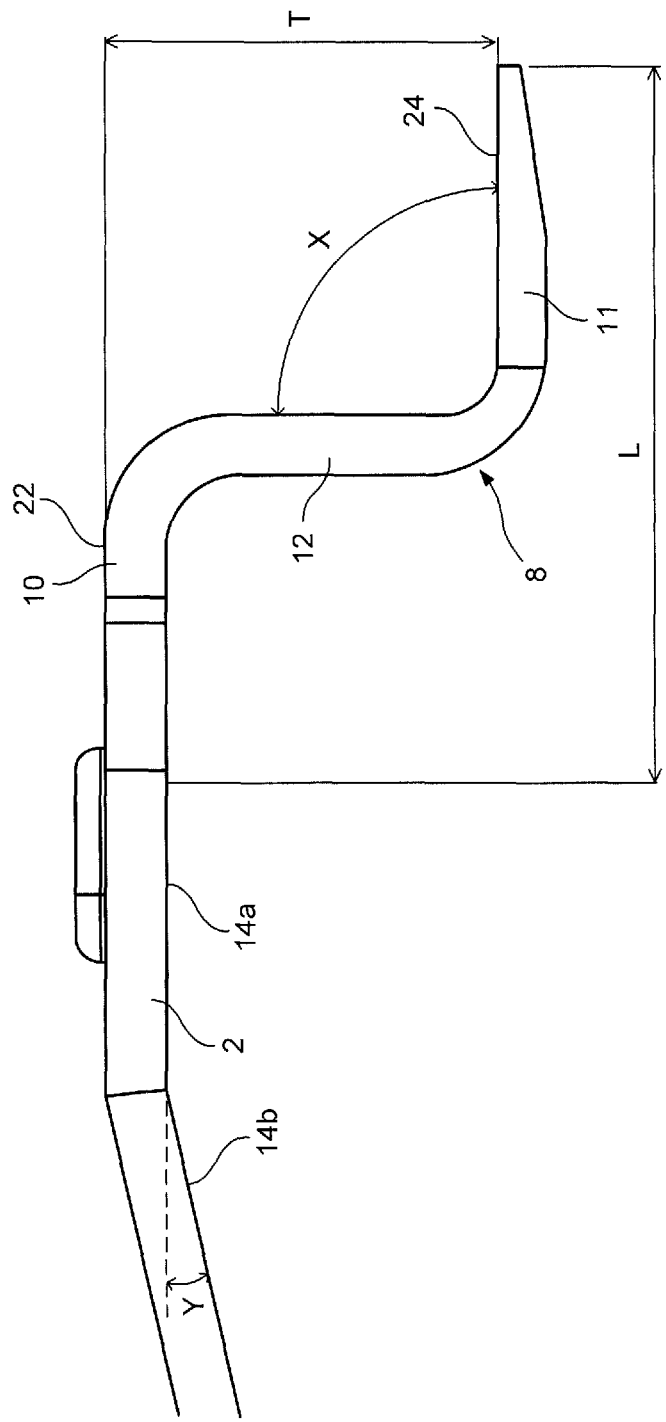
FIG. 3 illustrates a side plan view of the hook plate assembly in the direction of arrow A, as shown in FIG. 1.

The hook 8, as shown in FIGS. 1 and 3, includes a connecting portion 10 and a tip portion 11 connected to one another via a transverse portion 12. The connecting portion 10 is sized and shaped to be coupled to the connection section 6 of the bone plate 2 by inserting the connecting portion 10 of the hook 8 into the recess 17. Thus, the connecting portion 10 of the hook 8 is correspondingly circularly curved and has the same middle radius R as the recess 17. The circularly curved connecting portion 10 defines a first plane of the hook 8. The tip portion 11 and the transverse portion 12 of the hook 8 lie in a second plane that is orthogonal to the first plane defined by the circularly curved connection portion 10. The bone contacting surface 14 may have a lateral part 14a and a medial part 14b, the surfaces of which extend at an angle Y relative to each other. The angle Y can be any suitable angle chosen for anatomical reasons, for example, the angle can be 12°. The tip portion 11 may extend substantially parallel to the bone contacting surface 14, in particular the lateral part 14a, at the connection section 6 of the bone plate 2 and forms an extension of the bone plate 2 in a longitudinal direction of the bone plate 2. The connecting portion 10 and the tip portion 11 extend in opposite directions from the transverse portion 12 so that the hook 8 is substantially S-shaped. Since each of the connecting portion 10, the tip portion 11 and the transverse portion 12 extends along a different axis the hook 8 is three-dimensionally curved. The hook 8 is used to pull the clavicle into a position that is normally maintained by the conoid ligament and the trapezoid ligament.

The hook 8 may include a through hole 13 through a portion of the connecting portion 10 of the hook 8 which overlaps the connection section 6 of the bone plate 2. The through hole 13 may be sized and shaped to receive a bone screw therethrough and into the aperture 18 in the connection section 6 of the bone plate 2 to fix the hook 8 relative to the bone plate 2 and the clavicle. The hook 8 may be treated with a plastic coating. Due to the circularly curved configuration of the recess 17 and the connecting portion 10 of the hook 8, the hook 8 is rotatable relative to the bone plate 2 about an axis of rotation. As shown on FIG. 3, the axis of rotation extends through the lateral part 14a of the bone contacting surface 14 of the bone plate 2. The axis of rotation may be substantially orthogonal to the lateral part 14a of the bone contacting surface 14 of the bone plate 2. The hook 8 may rotate relative to the bone plate 2 at an angle of up to about 20° about the axis of rotation, in an anterior direction, as shown in FIGS. 4a to 4c. The connecting portion 10 may also include a raised section 26 extending about a periphery thereof for engagement by a portion of the fastening element 9, which fixes the hook 8 to the bone plate 2. The raised section 26 is defined by a lateral wall 28.

The hook 8 has a depth T measured from an upper surface 22 (e.g., facing away from the bone) of the connecting portion 10 to an upper surface 24 (e.g., facing away from the bone) of the tip portion 11 of the hook 8 which may range from about 18 mm to about 12 mm. In a preferred embodiment, the depth T will not exceed about 20 mm. Since the hook 8 is removable from the bone plate 2, hooks 8 with different depths T, e.g. of 12 mm, 15 mm and 18 mm may be included so that the user (e.g., surgeon) may select the hook 8 having a desired depth T, particularly suited for the patient. The depth T may be chosen by the user to, for example, avoid soft tissue irritation. Furthermore, the user may select a hook 9 having a desired angle X between the upper surface 22 of the tip portion 11 and the transverse portion 12. The angle X of hooks 8 may vary from between about 60° and about 120°. Similarly, hooks 8 having a range of different lengths L may be included so that the user may select a hook 8 having the desired length L. Any suitable length L may be provided and may be chosen by the user according to a patient's anatomy. For example, the length chosen may be according to the size of a patient, the shape of the clavicle or acromion, etc., and so that the hook plate assembly 1 does not irritate soft tissue or interfere with a patient's proximal humerus when in position. The length L may range from between about 20 mm to 50 mm.

The fastening element 9 may be screwed into the connection section 6 of the bone plate 2 and comprises a head 15 including a nose 19 extending transversely from a longitudinal axis of the fastening element 9. The fastening element 9 may be pre-assembled with the bone plate 2 to prevent loss of the fastening element 9 during the surgery. As shown in FIGS. 5a to 5c the fastening element 9 may be movable between three positions. In the first position shown in FIG. 5a, the fastening element 9 is positioned so that the nose 19 does not extend over the recess 17, permitting an in situ attachment and/or detachment of the hook 8 from the bone plate 2. Once the hook 8 is coupled to the bone plate 2 by inserting the connecting portion 10 of the hook 8 into the recess 17, the fastening element 9 may be moved to the second position, as shown in FIG. 5b, in which the fastening element is rotated about the longitudinal axis thereof such that the nose 19 is slid over the raised section 26 along the upper surface of the connecting portion 10 of the hook 8. The nose 19 abuts the raised section 26 to hold the hook 8 in the recess 17 and to prevent the hook 8 from slipping out of the recess 17. In this second position, the nose 19 extends over a portion of the raised section 26 and applies a small friction force in order to hold the hook 8 in the recess 17. Thus, when the fastening element 9 is in the second position, the hook 8 is rotatable relative to the bone plate 2, as described above. Once the hook 8 has been rotated to a desired position relative to the bone plate 2 and is correctly positioned under the acromion, the fastening element 9 may be rotated about the longitudinal axis thereof and moved to a third position, as shown in FIG. 5c. This rotation causes more of the nose 19 to be engaged with the raised section 26 thereby increasing the friction force to hold the hook 8 in a desired position and prevent further rotation of the hook 8 relative to the bone plate 2. Also, due to the screw holding the fastening element 9 to the bone plate 2, the rotation from the second position to the third position may also causes the nose 19 to move closer in a perpendicular direction to the upper surface 16 of the bone plate 2. This slight movement causes the nose 19 to apply more pressure on the raised section 26 to thereby increase the friction force between the hook 8 and the recess 17.

The hook plate assembly 1 may be configured in either a left side or a right side configuration. The curvature of the longitudinal section 20 of the bone plate 2, the recess 17 and the hook 8 may be respectively adapted such that the hook plate assembly 1 may be used on the patient's left or right side.

A thickness of the bone plate 2 may be about 3.5 mm with a thickness of 0.5 mm in the recess 17, while the thickness of the hook 8 may be about 3.0 mm with the raised section 26 having a thickness of 0.1 mm to 0.3 mm. Alternatively, the thickness of the bone plate 2 may be about 3.0 mm with a thickness of 0.5 mm in the recess 17, and the thickness of the hook 8 may be about 2.5 mm with the raised section 26 having a thickness of 0.1 mm to 0.3 mm. It will be understood by those of skill in the art, however, that the bone plate 2 and the hook 8 may have any of a variety of thicknesses so long as the thickness of the bone plate 2 and of the hook 8 are selected such that the connecting portion 10 of the hook 8 slightly protrudes from the upper surface 16 of the bone plate 2 in the raised section 26.

As described above, the hook assembly 1 may be used to treat a fracture of a clavicle, proximate a lateral end thereof. The method for treatment of fractures of the lateral end of the clavicle may be performed using a minimally invasive procedure. During such a procedure a small incision near the lateral end of the clavicle is performed and the fracture and/or the dislocation are reduced. The user (e.g., surgeon) may select a bone plate 2 having a desired length and a hook 8 having an appropriate hook size (e.g., length, angulation, depth). The bone plate 2 may be slid through the incision under the skin along the clavicle. Once the bone plate 2 has been positioned as desired, small incisions may be formed in the skin to advance bone screws through the plate holes 7 in the bone plate 2 and into the clavicle. The screws are then advanced through the plate holes 7 and into the clavicle to fix the plate 2 thereto. As described above, the fastening element 9 is attached to the bone plate 2 prior to implantation thereof. The fastening element 9 is moved to the first position so that the hook 8 may then be coupled to the bone plate 2 by inserting the connecting portion 10 of the hook 8 into the recess 17 of the connecting portion 6 of the bone plate 2. The fastening element 9 is turned from the first position to the second position to prevent disengagement of the hook 8 from the bone plate 2 while the tip portion 11 of the hook 8 is positioned below the acromion by rotating the hook 8 relative to the bone plate 2. The hook 8 is rotated until an optimal fit with the acromion is achieved. Once the hook 8 has been positioned as desired, the fastening element 9 is moved from the second position to the third position to fix the hook 8 relative to the bone plate 2. Finally, the incision is closed.

Before the incision is closed, if necessary, an additional bone screw may be advanced into the clavicle through the through hole 13 in the hook 8 and the aperture 18 in the bone plate 2 to provide further fixation of the hook 8 relative to the bone plate 2 and the clavicle.

According to an alternative exemplary method, the hook assembly 1 may be used in the standard way in which a user performs open surgery to achieve a desired open reduction and internal fixation. In the alternative exemplary method, the hook 8 may be attached to the bone plate 2 prior to the implantation thereof so that the clavicle fracture may be treated by forming a large incision near the lateral end of the clavicle. A desired bone plate 2 and hook 8 are selected and assembled by moving the fastening element 9 from the first position to the second position, as described above. The hook assembly 1 is then positioned along the clavicle once the fracture and/or the dislocation has been reduced. The hook 8 is rotated and positioned under the acromion and the bone plate 2 is pressed onto the clavicle. The fastening element 9 may be moved to the third position to fix the hook 8 relative to the bone plate 2. Bone screws are then advanced through the plate holes 7 in the bone plate 2 and into the clavicle. The incision may then be closed.

If it is determined that the position of the hook 8 is not appropriate, prior to closing the incision, the fastening element 9 may be moved to the second position after the bone screws have been advanced into the clavicle. The tip portion 11 of the hook 8 may then be positioned under the acromion in the optimal position and the fastening element 9 may be subsequently moved to the third position to fix the hook 8 relative to the bone plate 2. If necessary, an additional bone screw may be advanced into the clavicle through the through hole 13 in the hook 8 and through the aperture 18 in the bone plate 2.

As shown in FIGS. 6a-6c, a hook plate assembly 1' according to a further embodiment may be substantially similar to the hook plate assembly 1, comprising a bone plate 2' sized and shaped to be positioned over a lateral portion of a clavicle, a hook 8' couplable to the bone plate 2' to be positioned under the acromion and a fastening element 9' to rigidly fix the book 8' to the bone plate 2'. While the hook 8 is rotatable relative to the bone plate 2 in an anterior direction up to about 20° about an axis of rotation, the hook 8' is rotatable relative to the bone plate 2' in both an anterior and a posterior direction up to about ±20°. The hook assembly 1' may be used to treat clavicular fractures in a manner substantially similar to the method described above in regard to the hook assembly 1. Once the bone plate 2' has been positioned over the lateral end of the clavicle, however, the fastening element 9' is moved to the second position such that the hook 8' may be rotated and positioned under the acromion. The bone fastening element 9' may then be moved to the third position to fix the hook 8' relative to the bone plate 2'. Bone screws may then be inserted through holes 7' extending through the bone plate 2' to fix the hook assembly 1' to the bone.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A hook plate assembly, comprising:
   A) a bone plate extending along a longitudinal axis from a first end to a second end and including an upper surface configured to face away from a bone, a bone contacting surface, a plate hole extending therethrough from the upper surface to the bone contacting surface and a connection section arranged at the second end, the plate hole being sized and shaped to receive a bone fixation element therethrough, the connection section including a recess extending along a curved path from a first recess end to a second recess end, the first recess end being enclosed within the connection section and the second recess end being open through the second end of the bone plate;

B) a hook including a connecting portion extending along a curved path corresponding to the curved path of the recess, the connecting portion being sized and shaped to be received within the recess to connect the hook to the connection section of the bone plate, wherein the connecting portion slides within the recess to rotate along the curved path of the recess to adjust an angle of the hook relative to the plate; and C) a fastening element releasably coupling the hook to the bone plate and holding the hook in a desired position preventing further rotation of the connecting portion within the recess.

2. The hook plate assembly according to claim 1, wherein the fastening element is movable between a first, second and third position, the first position permits the connecting portion of the hook to be coupled to the connection section of the bone plate, the second position prevents an inadvertent decoupling of the bone plate and the hook while allowing a rotation of the hook relative to said the longitudinal axis of the bone plate within a predetermined range of angulation, the third position fixes the hook at a desired angle relative to the bone plate.

3. The hook plate assembly according to claim 1, wherein the connecting portion of the hook includes a through hole extending therethrough.

4. The hook plate assembly according to claim 1, wherein the hook comprises a raised section for engagement by the fastening element for releasably coupling the hook to the bone plate.

5. The hook plate assembly according to claim 1, wherein the hook is treated with a plastic coating.

6. The hook plate assembly according to claim 1, wherein the hook is rotatable relative to the bone plate about an axis of rotation which extends through the bone contacting surface.

7. The hook plate assembly according to claim 6, wherein the axis of rotation is orthogonal to the bone contacting surface.

8. The hook plate assembly according claim 1, wherein the connection section of the bone plate is angled relative to a remaining length of the bone plate.

9. The hook plate assembly according to claim 8, wherein the connection section is angled relative to the remaining length of the bone plate at an angle of 12°.

10. The hook plate assembly according to claim 1, wherein the hook is one of C-shaped and S-shaped.

11. The hook plate assembly according claim 1, wherein the fastening element is a screw including a head having a maximum height of 1.5 mm.

12. The hook plate assembly according to claim 1, wherein the connecting portion of the hook protrudes above the upper surface of the bone plate.

13. The hook plate assembly according to claim 1, wherein the recess extends along a circularly curved path and has a middle radius R extending along a longitudinal axis extending from a middle portion of the circularly curved path.

14. The hook plate assembly according to claim 13, wherein the connecting portion of the hook is circularly curved corresponding to the curvature of the recess.

15. The hook plate assembly according to one claim 1, wherein the hook is rotatable relative to the bone plate from 0° to 20°.

16. The hook plate assembly according to claim 1, wherein the hook is rotatable relative to the bone plate from 0° to ±20°.

17. The hook plate assembly according to claim 1, wherein the hook includes a tip portion which, when the hook is connected to the bone plate, extends from the second end of the bone plate one of parallel to and at an acute angle relative to the longitudinal axis of the bone plate, the hook being curved in a plane substantially orthogonal to the bone contacting surface.

18. The hook plate assembly according to claim 1, wherein the bone plate includes an aperture extending through the connection section to receive a bone fixation element therethrough.

19. The hook plate assembly according to claim 18, wherein the aperture extends through the recess and is circularly curved with a radius R.

20. The hook plate assembly according to claim 1, wherein the hook is three-dimensionally curved.

21. The hook plate assembly according to claim 1, wherein the plate hole is elongated and has a long axis extending along the longitudinal axis of the bone plate.

22. The hook plate assembly according to claim 21, wherein the plate hole includes an internal thread along one end of the long axis.

23. The hook plate assembly according to claim 1, wherein the bone plate is one of S-shaped and C-shaped in a plane substantially parallel to one of the upper surface and the bone contacting surface.

24. The hook plate assembly according to claim 1, wherein the recess extends along a plane extending parallel to the bone contacting surface.

25. The hook plate assembly according to claim 24, wherein the recess extends along the upper surface of the bone plate.

* * * * *